United States Patent
Symes et al.

(10) Patent No.: US 6,361,981 B1
(45) Date of Patent: *Mar. 26, 2002

(54) PRODUCTION OF AMMONIUM ACRYLATE

(75) Inventors: Kenneth Charles Symes, Keighley; Jonathan Hughes, Brighouse, both of (GB)

(73) Assignee: Ciba Specialty Chemicals Water Treatments Limited, Bradford (GB)

( * ) Notice: Subject to any disclaimer, the term of this patent is extended or adjusted under 35 U.S.C. 154(b) by 0 days.

This patent is subject to a terminal disclaimer.

(21) Appl. No.: 09/664,813

(22) Filed: Sep. 19, 2000

Related U.S. Application Data

(63) Continuation of application No. 08/930,832, filed as application No. PCT/GB96/03081 on Dec. 12, 1996, now Pat. No. 6,162,624.

(30) Foreign Application Priority Data

Dec. 12, 1995 (GB) .............................. 9525372
Dec. 12, 1995 (GB) .............................. 9525374

(51) Int. Cl.[7] .................................. C12P 7/62
(52) U.S. Cl. ..................... 435/135; 435/128; 435/183; 435/191; 435/227; 526/199; 526/317.1; 526/329.3
(58) Field of Search ................ 435/128, 135, 435/183, 191, 227; 526/199, 317.1, 329.3

(56) References Cited

U.S. PATENT DOCUMENTS 6,162,624 A * 12/2000 Symes et al. ............. 435/135

FOREIGN PATENT DOCUMENTS

EP 0 444 640 9/1991
JP 63-2596 1/1988
WO 97/06248 2/1997

OTHER PUBLICATIONS

Chemical Abstracts vol. 121, No. 21, Nov. 21, 1994.

Chemical Abstracts vol. 113, No. 19, Nov. 5, 1990.

Archives of Microbiology, vol. 155, 1990, Springer Verlag, pp. 13–17, XP002028294 Toru Agasawa et al.

Applied Microbiology and Biotechnology, vol. 34, 1990, Springer Verlag pp. 322–324, XP002028295 Toru Nagasawa et al.

Biotechnology and applied bi0chemistry, vol. 11, 1989, pp. 581–601, Goldlust et al.

Journal of Bacteriology, vol. 172, No. Sep. 9, 1990, pp. 4807–4815.

Biotechnology and applied biochemistry, vol. 15 1992, Stevenson et al. pp. 283–302.

* cited by examiner

*Primary Examiner*—Francisco Prats
*Assistant Examiner*—Kailash C. Srivastava
(74) *Attorney, Agent, or Firm*—David R. Crichton

(57) ABSTRACT

A solution having a high concentration of ammonium (meth)acrylate and which is substantially free of (meth)acrylonitrile is made by enzymatic hydrolysis of (meth)acrylonitrile in the presence of water using an enzyme that has Km for (meth)acrylonitrile below 500 $\mu$m and Ki for ammonium (meth)acrylate about 100,000.

17 Claims, No Drawings

PRODUCTION OF AMMONIUM ACRYLATE

This is a continuation of prior application Ser. No. 08/930,832 filed Apr. 27, 1998. Now, U.S. Pat. No. 6,162,624 which is a 371 of PCT/GB96/03081 filed Dec. 12, 1996.

This invention relates to processes for making aqueous solutions of ammonium acrylate and other acrylic monomers.

There is a major industrial need to produce aqueous acrylic acid, or a water soluble salt thereof such as ammonium acrylate or sodium acrylate, for instance for use as a polymerisable monomer, It is necessary that the aqueous solution should be as free as possible of impurities which are undesirable either from an environmental point of view or because they might interfere with subsequent polymerisation.

One common way of making acrylic acid industrially comprises hydrolysing acrylonitrile to form acrylamide and then hydrolysing the acrylamide to form ammonium acrylate or acrylic acid. Although most commercial processes of this type rely upon chemical hydrolysis, enzymatic hydrolysis is known for each stage (ie nitrile hydratase for converting nitrile to amide and amidase for converting amide to acid salt). The manufacture of acrylic acid by this technique is economically inconvenient, for instance because it requires an extensive amount of equipment for the two stages. Also extensive purification procedures are generally required. For instance it is essential to remove impurity amounts of acrylonitrile to very low levels and this may necessitate extensive distillation.

Another commonly used process for making acrylic acid is by hydration of propylene oxide. This avoids the need to conduct purification procedures in order to eliminate any acrylonitrile contamination but has the disadvantage that the process has to be conducted in complex, generally pressurised, apparatus.

There have been a few proposals in the literature for use of a nitrilase enzyme for converting aqueous acrylonitrile direct to aqueous ammonium acrylate. It is generally accepted that the direct conversion is more effective on aromatic than aliphatic nitrites, eg Stevenson et al, Biotech and Appl. Biochem. 15, 283–302 (1992).

In one example of EP-A-444640 acrylonitrile at a concentration of below 200 mM was hydrolysed using nitrilase catalyst to achieve almost quantitative conversion to acrylic acid, together with some acrylamide contamination.

In JP-B-632596 a 2% acrylonitrile solution is utilised in one example and in another example a 25% acrylonitrile solution is hydrolysed to a 32.9% ammonium acrylate solution. In a further example a 15% (meth) acrylonitrile solution is utilised to give a 23% ammonium (meth) acrylate solution.

In Biotech and Appl Biochem 11, 581 to 601 (1989) it is stated that the particular enzyme discussed in that article has Km for acrylonitrile of 17 mM. No process conditions are given but this value necessarily indicates that a substantial amount of acrylonitrile will remain in the product. The article indicates that 4–6% acrylamide is formed. The same article also indicates that the enzyme discussed in that article has a much higher activity for benzonitrile than for acrylonitrile.

In J Bacteriol September 1990 page 4807 to 4815 the properties of R rhodochrous K22 are analysed and it is stated that this has Km for acrylonitrile of 1.14 mM. This value also indicates the necessary presence of substantial amounts of acrylonitrile in the end product. There is no information given as to the concentration of ammonium acrylate which can be obtained but the article does note that enzyme activity is rapidly lost at above 55° C.

In Appl Microbiol Biotech 1990, 34, pages 322 to 324 a fed batch process of converting acrylonitrile to acrylic acid is described. The acrylonitrile has to be kept at a concentration below 200 mM (1.06%) and the product is said to contain 38% acrylic acid after 24 hours. The products were extracted by solvent extraction followed by evaporation and distillation.

These enzymic conversion processes provide a useful alternative to the two step enzymatic conversion (ie acrylonitrile to acrylamide and then acrylamide to ammonium acrylate) and the chemical conversion process, but all retain the requirement for extensive purification procedures to reduce acrylonitrile levels.

According to the invention, we make an aqueous solution containing at least 30% by weight (meth) acrylic acid or salt thereof and below 0.2% (meth) acrylonitrile by a process comprising providing water and (meth) acrylonitrile in an amount sufficient to provide, upon hydrolysis, a concentration of (meth) acrylic acid or salt thereof of at least 30% by weight and providing during the process in contact with the (meth) acrylonitrile, an enzyme for converting (meth) acrylonitrile to ammonium (meth) acrylate and which has Km for (meth) acrylonitrile below 500 $\mu$M and Ki for ammonium (meth) acrylate above 100,000 $\mu$M, allowing hydrolysis of (meth) acrylonitrile to occur to provide a reaction solution which has a concentration of (meth) acrylonitrile of below 0.2% and a concentration of ammonium (meth) acrylate of above 30% and recovering a solution having concentrations of ammonium (meth) acrylate of above 30% and acrylonitrile of below 0.2%.

Thus in the invention we use an enzyme which can scavenge (Seth) acrylonitrile to extremely low concentrations to produce ammonium (meth) acrylate even when the amount of ammonium (meth) acrylate or other (meth) acrylic acid salt present in the reaction solution can be very high. As a result we obtain, for the first time, a high concentration of ammonium (meth) acrylate or other (meth) acrylic acid monomer contaminated with only a very low amount of (meth) acrylonitrile. In particular, by using an enzyme which has a very low Km value we are able to achieve a very low (meth) acrylonitrile content in the final product and by using an enzyme which also has a high Ki value we are able to achieve this low concentration of (meth) acrylonitrile in the presence of a high concentration of ammonium (meth) acrylate.

It is very surprising that we can provide a process which can produce high concentration ammonium (meth) acrylate or other (meth) acrylic acid salt and very low concentration (meth) acrylonitrile. In particular it is surprising that we can achieve this using, as is preferred, a dilute concentration of acrylonitrile. By use of the invention it is even possible to achieve the desired product in a single stage in good yield and to excellent purity, with the need for purification to remove (meth) acrylonitrile thus avoided. It is particularly surprising that this can be achieved in a process which is conducted at a ratio of concentrations starting material:end product of <0.2:>30.

In the invention we provide (meth) acrylonitrile and water for reaction to (meth) acrylic acid or salt thereof by hydrolysis. It is possible to carry out the majority of the hydrolysis using chemical means to produce an aqueous solution containing (meth) acrylic acid (or salt thereof) and unreacted (meth) acrylonitrile. The defined enzyme is then provided in contact with the (meth) acrylonitrile and further hydrolysis of the unreacted (meth) acrylonitrile is allowed to occur until the reaction solution has a concentration of (meth) acrylonitrile of below 0.2% and a concentration of ammonium (meth) acrylate of above 30%.

The amount of (meth) acrylonitrile is usually below 0.1% and may be so low as to be non-detectable by convenient analytical techniques.

Processes of the invention may be carried out in two stages in a single reactor. Alternatively the chemical stage may take place in one reactor and the resultant solution containing dissolved (meth) acrylic acid or salt and residual (meth) acrylonitrile can be transferred to a bioreactor where reduction of residual (meth) acrylamide takes place on contact with the defined enzyme.

Preferably however substantially all hydrolysis of (meth) acrylonitrile is catalysed by the defined enzyme. In this case the solution produced contains at least 30% by weight ammonium (meth) acrylate. Thus preferably we charge a reactor with the acrylonitrile, enzyme and water and we recover the final solution.

We find that ammonium acrylate monomer produced by wholly enzymatic processes of the invention (bio-ammonium acrylate) shows excellent properties, equivalent to or better than the properties of monomers produced by alternative chemical routes, such as from acrylic acid derived from propylene oxide. Polymers produced using monomers made by the process of the invention also show excellent properties. The bio-ammonium acrylate made according to the invention may be converted into another chemical form, for instance acrylic acid or its sodium or other alkali metal salt or other related acrylic monomer and used as a starting monomer for the production of acrylic polymers. Alternatively it may be used without conversion, as ammonium acrylate. It may be used to form homopolymers or in combination with other monomers to produce copolymers.

In this specification, the invention will be discussed in the context of the preferred substantially enzymatic process for the production of ammonium (meth) acrylate, but it will be understood that the principles discussed are applicable to processes in which other (meth) acrylic acid salts, or (meth) acrylic acid itself, are produced and in which the first stage is by chemical hydrolysis of (meth) acrylonitrile.

The process of the invention can be operated as a one-stage process. In such a process a reactor is charged with water and with (meth) acrylonitrile in an amount sufficient to provide, upon hydrolysis, an ammonium (meth) acrylate concentration of at least 30% by weight and is also charged with a defined enzyme. Hydrolysis is then allowed to occur until the solution in the reactor has a concentration of (meth) acrylonitrile of below 0.2% (and often below 0.1%) and a concentration of ammonium (meth) acrylate of above 30%. The solution is then removed from the reactor.

A process of this type can be operated as a continuous process. In such a process (meth) acrylonitrile is fed into the continuous reactor to give a concentration in the reactor of (meth) acrylonitrile of below 0.2%, often below 0.1%, preferably below 0.05% (2, 1 and 0.5 g/l respectively). The concentration of ammonium (meth) acrylate in the reactor is maintained at 30 wt % or greater. Therefore material from the reactor can be continuously drawn off from the reactor to give a product which contains at least 30% ammonium (meth) acrylate and below 0.2% (meth) acrylonitrile. Usually the mixture is drawn off at the same rate as the rate of feed of reactants, so as to maintain a fixed working volume in the reactor.

Water is also a reactant and a solvent for the (meth) acrylonitrile and ammonium (meth) acrylate. Water can be included in the reactor in the full amount required at the beginning of the reaction. More usually however water may be fed into the reactor during the reaction. It can be fed in with the (meth) acrylonitrile in the form of an aqueous solution of (meth) acrylonitrile. The (meth) acrylonitrile solubility limit in the water at ambient temperature is about 7% weight/weight and the (meth) acrylonitrile solution is usually saturated. If (meth) acrylonitrile is added in the form of a solution it is often desirable to add (meth) acrylonitrile neat in addition to the solution. Neat (meth) acrylonitrile can be fed in liquid form or as (meth) acrylonitrile vapour. Water can be added to the reactor entirely separately from neat (meth) acrylonitrile.

Various reactor types are suitable for this process. They include continuous stirred tank reactors, draw-fill and loop type reactors and plug flow reactors. Suitable systems include a series of packed bed reactors into each of which is fed (meth) acrylonitrile and water. Reaction solution is passed from the first packed bed reactor to the second and then to the third and so on. Reaction solution containing at least 30 wt % ammonium (meth) acrylate and below 0.2 wt % (meth) acrylonitrile is drawn off from the final packed bed reactor. Fluidised bed reactors can also be used, in particular in place of packed bed reactors.

Alternatively a process of this one-stage type may be a fed batch type process. In such a process (meth) acrylonitrile is fed into the reactor and allowed to react to produce ammonium (meth) acrylate. This is done in such a way as to maintain the concentration of (meth) acrylonitrile between an upper and a lower concentration limit. The (meth) acrylonitrile may be fed continuously into the reactor to maintain a concentration within this range. Alternatively it may be fed to an extent that the concentration of (meth) acrylonitrile reaches the upper limit of the range. Feeding is then suspended until the concentration of (meth) acrylonitrile drops to the lower limit of the range, at which point further feeding is commenced to raise the concentration of (meth) acrylonitrile again. This process is continued until the concentration of ammonium (meth) acrylate has reached a predetermined level, which is at least 30 wt %.

The concentration of (meth) acrylonitrile in the fed batch reactor may be held at below 0.2% throughout the whole reaction, with both upper and lower limits of the chosen range being below this level. Alternatively the concentration may be allowed to rise above this level during the reaction or may be above this level throughout substantially the entire reaction. The upper limit is usually 1 or 2 wt % or less, often 0.5 wt % or less, preferably 0.2% or less. However, it is essential that at the end of the fed batch reaction the concentration of (meth) acrylonitrile is allowed to diminish to below 0.2%, preferably below 0.1% or 0.05%.

When the concentration of (meth) acrylonitrile is below 0.2% and the concentration of ammonium (meth) acrylate is above 30% the solution is removed from the reactor. A new fed batch may then be started.

Water may be added to the reactor before the reaction starts or may be added during the reaction, in the same way as for continuous processes above.

Suitable reactors for fed batch reaction include the same types as those useful for continuous reactors, as well as fed batch stirred tank reactors.

Continuous and fed batch processes are preferred according to the invention. However the invention also includes the use of batch processes as one-stage processes. In a batch process the reaction vessel is charged with sufficient (meth) acrylonitrile to provide a suitably high concentration of ammonium (meth) acrylate on reaction and left to react in the presence of the enzyme. The reaction is continued until the (meth) acrylonitrile diminishes to a predetermined level, which is always below 0.2% and often below 0.05%.

Suitable reactors for a batch reaction include a batch stirred tank reactor.

The process of the invention may on the other hand be carried out as a two-stage enzymatic hydrolysis process. In a process of this type, an initial stage is carried out during which hydrolysis of (meth) acrylonitrile occurs to an extent that either the percentage by weight of ammonium (meth) acrylate is less than 30% or is otherwise too low, or the percentage by weight of residual (meth) acrylonitrile is greater than 0.2 or other desired final concentration, or both. Normally ammonium (meth) acrylate is present in an amount of at least 30 wt % but the amount of residual (meth) acrylamide is greater than 0.2 wt %. This initial stage is carried out in a first reactor.

The reaction solution from this first reactor is then transferred to one or more subsequent reactors. In the further reactor or reactors, additional hydrolysis is catalysed by further enzyme of the defined type so as to produce an aqueous solution containing at least 30 wt % ammonium (meth) acrylate and not more than 0.2 wt % (meth) crylonitrile. Such further stages are often known as "polishing" stages.

Processes involving an initial stage and one or more further stages can be carried out as continuous, fed batch or batch processes. That is, the initial stage can be carried out as a continuous process, a fed batch process or a batch process in any of the ways described above. The resulting solution is then passed to a further polishing stage. In this polishing stage additional hydrolysis is catalysed by the defined enzyme so as to give a final product which has the required content of ammonium (meth) acrylate and (meth) acrylonitrile. This product is then removed from the final reactor.

In a preferred two-stage process, reaction mixture is enzymatically hydrolysed in a continuous or other reactor, to produce a product containing at least 30 wt % ammonium (meth) acrylate, and (meth) acrylonitrile in an amount of from around 0.5 wt % to saturation (which can be from around 4 wt % to around 7 wt %). This product is passed into a further stage for polishing, wherein the acrylonitrile concentration is reduced by enzymatic hydrolysis to below 0.2% and often below 0.1%, and the ammonium (meth) acrylate concentration is increased.

The further stage may consist of at least two reactors, such as tanks. The first reactor is filled with the reaction solution from the initial stage. As the first reactor is filled, the (meth) acrylonitrile is hydrolysed by the defined enzyme present in the reactor. When this first reactor is filled the final product, which has a content of (meth) acrylonitrile below 0.2 wt %, and often below detectable levels, is removed from the reactor. At this time filling of a second, usually identical, reactor is begun. This is filled in the same way and when it is full reaction mixture is pumped from the second reactor and filling of the first reactor begins again. Thus each reactor works in an alternative fed batch type manner.

An alternative polishing step could comprise a packed bed reactor or series of packed bed reactors containing the defined enzyme.

A further two-stage process comprises a packed bed reactor as the first stage. Water and (meth) acrylonitrile are sent into a cycle in which they are mixed in an in-line mixer and sent to the packed bed reactor. The product emerging from the packed bed reactor contains at least 30 wt % ammonium (meth) acrylate and (meth) acrylonitrile in an amount of usually from 0.5 wt % to saturation. Some of this product is sent to a polishing step and some is recycled into the continuous initial stage process.

A further two-stage process involves producing by a first stage a solution containing up to 30 wt % ammonium (meth) acrylate and at least 1 wt % (meth) acrylonitrile. This is sent distillation stage where the solution is concentrated to give a concentration of ammonium (meth) acrylate of from 35 to 40 wt %. This product is then sent to an enzymatic polishing stage in accordance with the invention to reduce the amount of (meth) acrylonitrile to below 0.2 wt %.

A polishing stage can be used with any of the initial stages described above which do not produce in that single stage a final product having the defined properties.

In a two-stage process the amount of (meth) acrylonitrile in the solution emerging from the first step is often from 0.5 to 7 wt %, for instance at least 1 wt % and can be up to around 3 or 4 wt %.

In these two-stage processes a particular surprising feature of the invention is the fact that it is possible to use an enzyme of the same type for both the initial stage and the polishing stage. Thus the enzyme is unusual in that it is capable of scavenging very low levels of (meth) acrylonitrile in the presence of very high levels of product (in the polishing stage), as discussed above. Further, however, most nitrilase enzymes tend to become deactivated in the presence of relatively high levels of (meth) acrylonitrile, for instance levels above 0.5 or 1 wt %, and in particular levels up to and around saturation. The enzyme used in the invention is capable of catalysing conversion in the relatively high (meth) acrylonitrile environment of the initial stage and in the very low (meth) acrylonitrile environment of the polishing stage.

In particular preferred enzymes for use in the process of the invention have half life as measured in an aqueous solution containing 120 to 175 mM acrylonitrile and 2,475 to 2,525 mM ammonium acrylate of at least 5 days. Preferably the half life is at least 7 days, more preferably at least 7.5 days. The exact content of acrylonitrile and ammonium acrylate may vary during the test but is always kept within the specified concentration limits. Acrylonitrile will be converted to ammonium acrylate by the nitrilase and the acrylonitrile concentration will thus reduce progressively. When the concentration reaches the lower limit of 125 mM, additional acrylonitrile is added to raise the concentration to the upper limit of 175 mM. Similarly the amount of ammonium acrylate is allowed to vary between the specified levels, with adjustment of ammonium acrylate concentration to prevent concentration going above the specified maximum of 200,525 mM.

In all processes of the invention the final concentration of (meth) acrylonitrile is below 0.2%, often below 0.15% or 0.1%, preferably below 0.05%. Preferably it is below 0.03%, more preferably below 0.02 or 0.01% and may be so low as to be substantially undetectable.

The final concentration of ammonium (meth) acrylate is at least 30% by weight, often at least 35% by weight, preferably at least 40 or 45% by weight. Maximum concentration of ammonium (meth) acrylate is usually 48 to 50 wt %, since above these levels the ammonium (meth) acrylate tends to precipitate out of solution.

The enzyme nay be included in the process in any suitable form. It may be used in the pure form, having been extracted from a cultured microorganism before use as a catalyst. The extraction method used should ensure that the activity and stability of the enzyme are not lost.

It may also be used in a semi-pure form, for instance as liquid culture or a bacterial cell fraction such as intact cells or crushed cells. It may be used in the form of a crude, impure enzyme solution. It may be supported or immobilised on a carrier, such as a cross-linked polymeric matrix, eg cross-linked polyvinyl alcohol or cross-linked polyacrylamide. It may be used in the form of non-swollen particles with surface bound enzyme. Preferably it is used in the form of intact bacterial cells or supported in a cross-linked polymeric matrix.

We find that for fed batch type reactions in particular it is advantageous to use enzyme in pure or semi-pure form as free cells. Use in this form avoids the necessity to immobilise the cells on a carrier but we find it does not lead to reduced stability on storage or in the reaction mixture to an excessive extent.

For continuous type processes we prefer to use enzyme in the immobilised form, since this tends to give greater long term stability in the reactor which is used. In particular, we have found that in some circumstances enzyme in immobilised form is as stable in the reaction mixture as it is on storage. Separation of catalyst from final product is also generally easier.

When the enzyme is being immobilised, in particular in the form of polymer beads, we find that production of polymer beads of larger size improves enzyme stability during polymerisation. In particular beads of size greater than 850 µm, preferably greater than 1 mm, are preferred.

Polymeric matrix can be produced in any manner, for instance by bead or suspension polymerisation. Addition of viscosifier to the monomer mixture can also be useful.

We find that stability of the enzyme during production is greatest at low cell loading, ie weight percentage of dry cells based on polymer matrix, in particular below 5%, preferably below 1%, for instance around 0.5 wt %. However, stability can also be achieved by using low polymerisation temperature, for instance below 30 or 20° C., often below 15° C. This can be used in combination with a higher cell loading, for instance at least 4 wt %, preferably at least 5 wt %, for instance around 6.5 or 6.8 wt %.

In the preferred process the enzyme is included in the reaction mixture so as to provide the desired activity in the reactor. Usually the form of catalyst added to the reactor has an activity of from 50 to 100,000 nitrilase units per gram, typically 500 to 5000 nitrilase units per gram, where one nitrilase unit is defined as conversion of acrylonitrile to ammonium acrylate at the rate of 1 µmol/min at 30° C., pH7 and 50mM acrylonitrile in 50mM phosphate buffer. The catalyst may be in the form of bacterial cells or, more usually, immobilised in a polymer gel matrix. The catalyst having the defined activity is included in the reactor in an amount of from 1 to 50% by weight of reaction mixture.

In particular, it is preferred that enzyme is added to the reaction mixture to give an activity of 3000 to 50,000 nitrilase units per litre of reaction mixture.

In two-stage processes of the invention we find it desirable to include larger amounts of enzyme catalyst in the polishing stage than in the initial stage.

In preferred processes the full amount of required enzyme is usually charged to the relevant reactor at the beginning of the reaction, that is before addition of (meth) acrylonitrile reactant or reaction solution. However, it is also possible to carry out the preferred process by adding additional enzyme to the relevant reactor during the reaction, either continuously or periodically.

The reaction is carried out in aqueous solution. Generally the only components of the aqueous solution are water, enzyme (including bacterial cells, polymer matrix etc), (meth) acrylonitrile and ammonium (meth) acrylate.

The reaction may be carried out for any suitable time. continuous reaction may be carried out for as long as 10 ours, generally at least 20 or 30 hours, often 50 or 60 ours or more. The duration of a continuous reaction generally tends to depend at least in part upon the stability of the enzyme in the reaction solution. A highly stable enzyme enables continuous reactions to be carried on for a significant period of time without the necessity to add additional fresh enzyme to the reaction mixture.

Fed batch processes and batch processes generally take from 1 to 24 hours, for instance about 5 hours. The duration of this type of reaction depends upon the activity of the enzyme, and the rate at which it converts (meth) acrylonitrile to ammonium (meth) acrylate. An enzyme with a high Ki value for ammonium acrylate will allow rapid conversion of acrylonitrile even when the product concentration has reached 35% or even 40%, unlike the nitrilase described in Appl. Microbiol. Biotech. 1990, 34, pages 322 to 324, where pronounced product inhibition is evidenced by a lower conversion rate apparent as low as 25 to 30% ammonium acrylate.

The processes of the invention are generally carried out at a temperature of 5 to 70° C., preferably 20 to 60° C. We find that we can, by using low reaction temperatures, reduce loss of enzyme activity without significantly reducing yield of ammonium (meth) acrylate. For instance temperatures below 30° C. and, especially, below 20° C. are useful. The reaction temperature can be below 15° C. and even as low 10° C.

Conditions of pH are usually 3 to 9.5, preferably 5 to 9, more preferably 6 to 8.

The very low concentrations of (meth) acrylonitrile present in the reactor necessitate careful control of reactant concentration, in particular for fed batch and, especially, continuous processes.

Measurement and control of (meth) acrylonitrile concentration can be performed in any conventional manner (eg spectroscopic or chromatographic) on the liquid phase but a particularly convenient and rapid method is the detection of (meth) acrylonitrile in the headspace gas in equilibrium with the reaction mixture. This can be done using U.V. analysis.

If the reactor does not have a headspace, analysis can be carried out on any vapour which can be held in equilibrium with the reaction mixture, for instance by means of a bleed.

A further suitable monitoring technique is with the use of conductivity. Portions of the reaction mixture are removed, for instance by sampling or by means of a bleed. We have found that the relationship between conductivity and concentration of ammonium (meth) acrylate is very sensitive and is essentially linear at low concentrations of ammonium (meth) acrylate, for instance below about 20 wt %. Since the processes of the invention will tend to be carried out at concentrations higher than this, the reaction solution sample is diluted down so that the concentration of ammonium (meth) acrylate is within this sensitive linear region.

Conductivity is then used to measure the level of ammonium (meth) acrylate very accurately. The percentage of (meth) acrylonitrile is then established using material balance calculation.

We also find that at high concentrations, for instance above 30 wt %, of ammonium (meth) acrylate, (meth) acrylonitrile present has have an observable effect on the conductivity. It is also possible to use this effect to assess the levels of (meth) acrylonitrile in the reaction mixture.

In the processes of the invention, in particular in continuous processes and often in fed batch processes, it is very desirable to maintain a (meth) acrylonitrile concentration which is low. In general it is important to minimise localised regions of very high concentration of (meth) acrylonitrile, for instance where (meth) acrylonitrile is fed into the reactor. In general catalyst life is maximised at low (meth) acrylonitrile concentration. If average concentration is very low, transient contact with concentrations of (meth) acrylonitrile above 0.2% or even 1 or 2% may be tolerated. Likewise temporary variations in concentration with time may be tolerated if the average is low and the variation lasts for only a very short time.

The incidence of local high concentrations of (meth) acrylonitrile can be reduced by suitable choice of addition devices and by ensuring adequate stirring is maintained in the reactor.

Control of fed batch reactions can be carried out using programmed control devices, for instance computer controlled devices. Such a control device is programmed to feed in (meth) acrylonitrile, in liquid or vapour form, at a predetermined rate.

Fed batch and continuous reactions, in particular those carried out in a continuous stirred tank reactor, can be controlled using a feedback system. Analysis of the reaction mixture can be carried out, for instance on the headspace or in any other manner described above, and the resulting measurements used to control the feed of (meth) acrylonitrile, as liquid or vapour, into the reactor.

Control may be effected by means of cycling gas or immiscible liquid through the reactor. The gas may be for instance (meth) acrylonitrile vapour or (meth) acrylonitrile vapour mixed with other gas. The immiscible liquid can be any liquid not miscible with the reaction mixture. Again, (meth) acrylonitrile can be dissolved in or mixed with this immiscible liquid. The gas or immiscible liquid is bubbled through the reaction mixture, passing (meth) acrylonitrile into the mixture. The bubbles of gas or immiscible liquid pass through the reaction mixture, usually upwards since the gas or immiscible liquid is often chosen to be less dense than the reaction mixture. It can then be drawn off and analysed. Results of this analysis can be used to control the feeding of the gas or immiscible liquid into the reaction mixture. The gas or immiscible liquid can also carry water into the reaction mixture. Such a system can be used in particular for continuous reactions, in particular in continuous stirred tank reactors, and fed batch reactions.

The reaction mixture itself may be cycled, being drawn off through a loop and returned to the reaction mixture. The loop can be connected to a source of (meth) acrylonitrile, and often water. Analysis can be carried out in line in the loop or on the headspace to allow control of reactant addition to the loop. If the reaction is a continuous one there may be provided a bleed by which reaction mixture can be removed from the loop.

In all cases the reactor can be provided with a stirrer, although this is not always necessary.

For continuous reactions any suitable method of drawing off the reaction mixture can be used. Suitable method include a bleed as described above and a weir which the reaction mixture can overflow and pass out of the reactor.

The enzyme must have Km for (meth) acrylonitrile, that is whichever of acrylonitrile and (meth) acrylonitrile is being converted, below 500 $\mu$m and Ki for ammonium acrylate or ammonium (meth) acrylate, whichever is being produced, above 100,000 $\mu$M. In this specification Km and Ki are measured under conditions in which the enzyme obeys Michaelis-Menten kinetics, in particular at pH 7. A preferred measurement technique uses enzyme in whole cell form in 50 mM sodium phosphate buffer at pH 7 and 30° C. and using concentrations of acrylonitrile from 0.01 to 0.5 mM (for Km) and using 1.2 M ammonium acrylate and 0.079 to 0.554 mM acrylonitrile (for Ki).

Preferably Km is below 300 $\mu$M, more preferably below 100 $\mu$M, most preferably below 60 $\mu$M. A preferred enzyme on which we have conducted initial experiments has Km 30.6 $\mu$M in whole cell form and we anticipate that the application of standard techniques and selection procedures, eg, those described for amidase in Silman et al., (1989) J.Gen. Microbiol., 135 3153–3164 and those described for lactate dehydrogenase by Wagner (1990) Tibtech., 8 263–270 will yield enzyme having Km values down to 9.4 and even 3.8 $\mu$M.

Ki is preferably at least 150,000 or 200,000, more preferably at least 250,000 $\mu$M. A preferred enzyme on which we have conducted initial experiments has Ki which we have estimated to be 309,000 $\mu$M. It is envisaged that the standard techniques and selection procedures such as those mentioned for Km above will yield enzyme having Ki up to 300,000 $\mu$M or even 800,000 $\mu$M or greater.

The ratio Ki/Km is generally at least 200, preferably at least 300, more preferably at least 500, in particular at least 1,000. Enzymes used in the process of the invention can have a ratio Ki/Km of at least 5,000, even 9,000 or greater and an enzyme on which we have conducted initial experiments has a value of this ratio of greater than 10,000.

A particularly preferred enzyme for use in the process of the invention is a new microorganism which we have isolated. It is a strain of *Rhodococcus rhodochrous* and has been deposited at NCIMB on Aug. 8, 1995 under accession number NCIMB 40757. Another preferred enzyme is a strain of *Rhodococcus rhodochrous* deposited by us at NCIMB on Dec. 11, 1996 with the accession number NCIMB 40833. Accordingly, a preferred aspect of the invention is a process in which the enzyme is one obtainable from a microorganism having the characteristics of *Rhodococcus rhodochrous* NCIMB 40757 or NCIMB 40833 or a mutant or variant of either of these.

These microorganism, and the nitrilase enzymes they produce are discussed in our copending international application number . . . (reference 60/3574/03) filed today, claiming priority from British Patent Application No. 9525372.0.

EXAMPLE 1

The original isolate of the strain of *Rhodococcus rhodochrous* deposited at the National Collection of Industrial and Marine Bacteria under the culture collection number NCIMB 40757 containing nitrilase enzyme or in which nitrilase enzyme can be induced is transferred into an Erlenmeyer flask containing the liquid culture medium shown in the table below.

| Component | Amount Present/litre |
|---|---|
| $K_2HPO_4$ | 7 g |
| $KH_2PO_4$ | 3 g |
| Sodium Acetate | 5 g |
| Acetonitrile | 2 g |
| $MgsO_4.7H_2O$ | 1 g |
| $CaCl_2.6H_2O$ | 0.2 g |
| Vitamins | 0.1 mL |
| Trace Metals | 1 mL |

The Erlenmeyer flask is incubated with agitation for 24 hours. The cells are then separated from the liquor, resuspended in 50 mM pH 7 sodium phosphate buffer and then separated from the buffer. A portion of the cells are stored frozen at −20° C. and the remainder is resuspended in 50 mM pH 7 sodium phosphate buffer containing 50 mM acrylonitrile. The specific nitrilase activity of the cells was determined to be 1060 μmoles/minute/g dry weight of cells.

The cells were then suspended in pure water at 30° C. Acrylonitrile was added periodically to the cell suspension to raise the acrylonitrile concentration to 190 mM. Samples were taken before each addition to determine the acrylonitrile, acrylamide and ammonium acrylate concentrations in the cell suspension. The table below shows the initial, maximum and final specific nitrilase activity, the final ammonium acrylate concentration and the time taken to reach that concentration.

| | |
|---|---|
| Initial specific enzyme activity (μmoles/min/g) | 518 |
| Final Ammonium Acrylate concentration (M) | 5.68 |
| Time taken to reach above concentration (hours) | 6.7 |
| Maximum specific enzyme activity (μmoles/min/g) | 901 |
| Specific enzyme activity upon batch completion (μmoles/min/g) | 122 |

Cell material was removed from the ammonium acrylate solution by centrifugation and filtration and the concentration of acrylonitrile, acrylamide and ammonium acrylate determined is shown in the table below.

| Monomer | Concentration |
|---|---|
| Acrylonitrile | Below the detectable limit |
| Acrylamide | 0.023 M |
| Ammonium Acrylate (wt %) | 50.5 wt % |

A further reaction carried out in the same way gave acrylamide concentration of 0.15 wt % and ammonium acrylate of 46 wt % with acrylonitrile below the detectable limit.

EXAMPLE 2

A continuous process of the invention is conducted using an enzyme such as described in Example 1. The enzyme is encapsulated in polymer beads to provide immobilised cells. These beads of immobilised cells are transferred to a reactor and suspended in a solution of 33 wt % ammonium acrylate and 3.6 wt % acrylonitrile at 20° C. Through the action of the immobilised catalyst the reactor ammonium acrylate concentration is allowed to rise to 35 wt %. Separate feeds of acrylonitrile and water are then automatically fed into the reactor to maintain the ammonium acrylate concentration at between 33 and 35 wt % and the acrylonitrile concentration at between 2.4 and 3.6 wt %. During operation a bleed of the acrylonitrile/ammonium acrylate solution and the bead material is continuously drawn from the reactor to maintain a constant reactor working volume. The reactor contents then enter a cyclone where the beads are separated and returned to the reactor. The product stream is then fed to one of a pair of polishing tanks. These tanks also contain beads of immobilised enzymatic material and at any one stage one tank is filling with the ammonium acrylate solution contaminated by acrylonitrile while the other is maintained for enzymatic hydrolysis conditions. After enzymatic hydrolysis has been conducted to a level which reduces the acrylonitrile to substantially non-detectable levels, that tank is emptied through a filter by which the beads containing enzyme and other solid components are separated from the solution of 39% ammonium acrylate which is substantially free of acrylonitrile.

EXAMPLE 3

A repeated fed-batch process of the invention is conducted using an enzyme as described in Example 1. The enzyme is encapsulated in polymer beads to provide immobilised cells. The beads of immobilised cells are transferred to a reactor and suspended in water at 20° C. and acrylonitrile is added to give a concentration of 1.2 wt %. The nitrile of the immobilised cells catalyse the hydrolysis of the acrylonitrile to produce ammonium acrylate. When the reactor acrylonitrile concentration is reduced to 0.9 wt % further acrylonitrile is automatically added to the reactor to raise the acrylonitrile concentration again to 1.2 wt %. This automatic feeding procedure continues until the reactor ammonium acrylate concentration has rise to 43.5 wt %. Upon completion of the batch the acrylonitrile feed ceases and the remaining acrylonitrile within the reactor is allowed to be converted to ammonium acrylate until the ammonium acrylate concentration is 45 wt % and the acrylonitrile concentration is substantially zero.

The ammonium acrylate solution produced is drawn off from the reactor and filtered to remove the cell material and immobilised biocatalyst. This material is then returned to the reactor which is then recharged with water at 20° C. and the process repeated.

What is claimed is:

1. A process for making an aqueous solution containing at least 30% wt (meth) acrylic acid or salt thereof and below 0.2% (meth) acrylonitrile comprising providing water and (meth) acrylonitrile in an amount sufficient to provide, upon hydrolysis, a concentration of (meth) acrylic acid or salt thereof of at least 30% wt and providing during the process, in contact with the (meth) acrylonitrile, an enzyme which converts (meth) acrylonitrile to ammonium (meth) acrylate and which has Km for (meth) acrylonitrile below 100 μM and Ki for ammonium (meth) acrylate above 100,000 μM, allowing hydrolysis of the (meth) acrylonitrile to occur until the reaction solution has a concentration of (meth) acrylonitrile of below 0.2% and a concentration of ammonium (meth) acrylate of above 30%, and recovering a solution having concentrations of ammonium (meth) acrylate of above 30%, and acrylonitrile of below 0.2%.

2. A process according to claim 1 in which (meth) acrylonitrile is subjected to chemical hydrolysis to provide a solution containing ammonium (meth) acrylate and acrylonitrile and the resultant solution is then contacted with the said enzyme and hydrolysis of the (meth) acrylonitrile is allowed to occur until the reaction solution has a concentration of (meth) acrylonitrile of below 0.2%.

3. A process according to claim 1 in which substantially all the hydrolysis of the (meth) acrylonitrile is by enzymatic hydrolysis with the said enzyme.

4. A process according to claim 3 in which a reactor is charged with the said enzyme and with water and with (meth) acrylonitrile in an amount sufficient to provide, upon hydrolysis, a concentration of ammonium (meth) acrylate of at least 30% wt and enzymatic hydrolysis is allowed to occur until the solution has a concentration of (meth) acrylonitrile of below 0.2% and a concentration of ammonium (meth) acrylate of above 30%.

5. A process according to claim 4 in which the final concentration of (meth) acrylonitrile is below 0.1%.

6. A process according to claim 4 in which Ki is at least 200,000 μM.

7. A process according to claim 4 in which the ratio Ki/Km is at least 5,000.

8. A process according to claim 4 in which the enzyme is obtained by culturing a microorganism deposited under the name of *Rhodococcus rhodochrous* NCIMB 40757 or NCIMB 40833.

9. A process according to claim 4 conducted by charging the reactor during the process with the enzyme, the water and the (meth) acrylonitrile and allowing hydrolysis to occur in the reactor and then removing the solution from the reactor.

10. A process according to claim 4 conducted as a two-stage enzymatic hydrolysis process wherein, during the first stage, hydrolysis of (meth) acrylonitrile occurs to an extent such that either the percentage by weight of ammonium (meth) acrylate is less than the desired final concentration or the percentage of residual (meth) acrylonitrile is greater than the desired final concentration, and this solution is then transferred to one or more subsequent reactors where it is subjected to further enzymatic hydrolysis to provide the desired final solution which is recovered.

11. A process according to claim 10 in which a reaction mixture comprising water and (meth) acrylonitrile is enzymatically hydrolysed in a continuous reactor to produce a product containing at least 30% by weight ammonium (meth) acrylonitrile and (meth) acrylonitrile in an amount of from 0.5% to saturation, and this product is then transferred to a subsequent reactor where the (meth) acrylonitrile concentration is reduced by enzymatic hydrolysis to below 0.1% and the ammonium (meth) acrylate concentration is increased.

12. A process according to claim 10 in which the subsequent reaction is conducted utilising at least two subsequent reactor vessels which are operated in an alternating fed batch manner.

13. A process according to claim 10 in which the first stage is conducted in a packed bed reactor to produce a solution containing 0.5% to saturation (meth) acrylonitrile and some of this solution is subjected to the further enzymatic hydrolysis while the remainder is recycled.

14. A process according to claim 10 in which the solution obtained by enzymatic hydrolysis in the first stage is subjected to distillation before being subjected to the second stage enzymatic hydrolysis.

15. A process according to claim 10 in which the same enzyme is used throughout the process.

16. A process according to claim 1 in which control of the process comprises detection of (meth) acrylonitrile, in the headspace of the reactor or reactors in which the enzymatic hydrolysis is conducted.

17. A process according to claim in which control of the reactor comprises diluting the concentration of this solution to below 20% ammonium acrylate and measuring the conductivity of the diluted solution.

* * * * *